United States Patent [19]
Au et al.

[11] Patent Number: 5,386,018
[45] Date of Patent: Jan. 31, 1995

[54] PROCESS OF PREPARING N-SUBSTITUTED ALDONAMIDES

[75] Inventors: Van Au, Congers, N.Y.; Bijan Harichian, South Orange; Michael I. Hill, Ridgewood, both of N.J.; Mikhail Raykh, Brooklyn, N.Y.; Jerry J. Krupa, Rockaway Township, Morris County, N.J.

[73] Assignee: Lever Brothers Company, Division of Conopco, Inc., New York, N.Y.

[21] Appl. No.: 147,699

[22] Filed: Nov. 4, 1993

Related U.S. Application Data

[63] Continuation-in-part of Ser. No. 23,529, Feb. 26, 1993, and a continuation-in-part of Ser. No. 958,402, Oct. 8, 1992, Pat. No. 5,296,588, each is a continuation-in-part of Ser. No. 816,422, Dec. 31, 1991, abandoned.

[51] Int. Cl.$^6$ .......................... C07G 3/00; C07H 15/04
[52] U.S. Cl. .................... 536/185; 536/1.11; 536/4.1; 536/17.9; 536/53; 536/22.1; 536/124
[58] Field of Search ................ 536/17.9, 1.11, 4.1, 536/53, 54, 18.5, 124, 22.1

[56] References Cited

U.S. PATENT DOCUMENTS

| | | | |
|---|---|---|---|
| 2,752,334 | 6/1956 | Walton | 536/53 |
| 3,862,005 | 1/1975 | Miyake et al. | 435/874 |
| 4,345,031 | 8/1982 | Coppens | 435/137 |
| 4,390,451 | 6/1983 | Havinga et al. | 252/311 |
| 5,008,247 | 4/1991 | Meinetsberger | 536/53 |

FOREIGN PATENT DOCUMENTS 550106 7/1993 European Pat. Off. .

*Primary Examiner*—Herbert J. Lilling
*Attorney, Agent, or Firm*—Rimma Mitelman

[57] ABSTRACT

N-substituted aldonamides are synthesized by the reaction of alkylamines and aldonolactone. Commercially available sources of aldonolactones (e.g., lactobiono-1,5-lactone) include aldonic acid (e.g., lactobionic acid). The presence of the acid leads to the formation of an ammonium salt impurity. The ammonium salt formation during the synthesis of N-alkyl aldonamides was minimized by the addition of an external acid. External acids and, optionally, emulsifiers were utilized to substantially reduce or eliminate the formation of an ammonium salt and to obtain N-substituted aldonamides of high purity.

21 Claims, No Drawings

PROCESS OF PREPARING N-SUBSTITUTED ALDONAMIDES

This is a continuation-in-part of a copending application Ser. No. 08/023,529, filed Feb. 26, 1993, which is a continuation-in-part of Ser. No. 07/816,422, filed Dec. 31, 1991, now abandoned, and this application is also a continuation-in-part of a copending application Ser. No. 07/958,402 filed Oct. 8, 1992, now U.S. Pat. No. 5,297,588, which is a continuation-in-part of Ser. No. 071816,422, filed Dec. 31, 1991, now abandoned.

FIELD OF THE INVENTION

The invention relates to an improved process of preparing N-substituted aldonamides.

RELATED ART

An aldonamide is defined as the amide of an aldonic acid and an aldonic acid in turn is defined as a sugar substance (e.g., any cyclic sugar) in which the aldehyde group (generally found at the $C_1$ position on the sugar) has been replaced by a carboxylic acid. Aldonamides may be based on compounds comprising one saccharide unit (e.g., gluconamide), two saccharide units (in which case aldonamides are termed aldobionamides, e.g., lactobionamide or maltobionamide) or they may be based on compounds comprising more than two saccharide units, as long as the polysaccharide has a terminal sugar unit with an aldehyde group available for oxidation.

Walton et al. (U.S. Pat. No. 2,752,334) discloses a process for the preparation of the N-substituted lactobionamides by reacting the corresponding organic primary or secondary amine with lactobiono-1,5-lactone. The reaction is effected by heating the reactants with a solvent in the case of the amines having a higher boiling point. However, the use of a solvent and lower temperature is said to give better yields with less chance of decomposition in the course of the reaction and therefore a purer product. Reaction temperatures within the range from 65° C. to 140° C. are said to be preferred. Yields of from 70% to 75% were reported.

Kobayashi et al., "Synthesis and Functions of Polystyrene Derivatives Having Pendant Oligosaccharides," Polymer Journal, Vol. 17, No. 4, 567–575 (1985), describe a process wherein a lactone is dissolved in refluxing methanol and a solution of amine in ethanol is added. The mixed solution is refluxed for two hours. 82% yield was reported.

Williams et al., "A new Class of Glycolipids: Synthesis, Characterization, and Interaction with Lectins," Archives of Biochemistry and Biophysics, Vol. 195, No. 1, June, 145–151, 1979, describe a process wherein a lactone was dissolved in methanol by gentle heating, an amine was added, and the reaction mixture was stirred overnight at room temperature. 70% yield was reported.

Ziegast et al., "Coupling of Mono- and Oligosaccharides to δ-w-diamino substituted Poly(oxyethylene) and Multifunctional Amines by Amide Linkage", Makromol Chem., Rapid Commun. 5,313–379 (1984) disclose the procedure for coupling of carbohydrates to various compounds: saccharide is converted into the aldonic acid lactone via electrolytic oxidation and subsequent binding to an amino group containing carrier by amide linkage. The reaction according to Ziegast et al. requires an excess of lactone, which is subsequently separated by using relatively strong basic ion exchange column. Ziegast et al. employ an excess of lactone and conduct the reaction at 70° C. or above.

Aldonamides are carbohydrate-based molecules and, as such, represent a source of renewable raw materials that are synthetically versatile and environmentally friendly. Aldonamides have useful physical Properties (e.g., surfactancy) which makes them suitable for many applications in personal care, dental, detergent and cosmetic areas. Surfactant compositions incorporating aldonamides have been described in a co-pending commonly assigned application, Ser. No. 07/981,737, incorporated by reference herein, it is possible to attain aldonamides as white crystalline solid. In prior filed commonly assigned patent applications Ser. No. 07/816,422, Ser. No. 08/023,529, and Ser. No. 07/958,402, a process for preparation of aldonamides has been described, which involved a reaction of aldonolactone with an alkylamine in an organic solvent (e.g., methanol). Unfortunately, commercially available sources of aldonolactones (e.g., lactobiono-1,5-lactone) contain a substantial amount of aldonic acid (e.g., lactobionic acid) as an impurity. The presence of an aldonic acid in a starting material leads to the formation of an ammonium salt which needed to be removed by passing the reaction product solution through an anionic exchange column (Ser. No. 07/816,422 and Ser. No. 08/023,529) or by treating the reaction product solution with a solid base (Ser. No. 07/958,402).

Accordingly, it is an object of the invention to provide an improved process of manufacturing N-substituted aldonamides.

It is another object of the invention to provide a process of preparing N-substituted aldonamides which avoids or substantially minimizes the formation of an ammonium salt.

It is yet another object of the invention to increase the yield of N-substituted aldonamides.

These and other objects of the invention will become more apparent from the detailed description and examples that follow.

SUMMARY OF THE INVENTION

The above objects are accomplished by the present invention which includes a process of preparing an N-substituted aldonamide, the process including the steps of:

i) preparing a homogeneous mixture comprising an aldonocompound, an external acid, an organic polar solvent comprising a solvent having an alcohol functionality, and an amine $HNR^1R^2$, wherein $R^1$ and $R^2$ are the same or different and may contain heteroatoms and are selected from the group consisting of hydrogen, an aliphatic hydrocarbon radical, an aromatic radical, a cycloaliphatic radical, an amino acid ester, an ether amine and mixtures thereof, except that $R^1$ and $R^2$ are not both hydrogen at the same time; and ii) reacting the homogeneous mixture at a temperature not greater than 100° C. to obtain the aldonamide.

The term "aldonocompound" as used herein means an ingredient selected from the group consisting of an aldonolactone, an aldonic acid and mixtures thereof.

The term "external acid" as used herein means any acid that is not an aldonic acid.

The present invention is based in part on the discovery that the inclusion of an external acid into the reaction mixture during the preparation of aldonamides substantially minimized or eliminated the formation of an ammonium salt.

In the preferred embodiment of the present process the order of addition of various ingredients is as follows:
(a) an aldonocompound is premixed with an organic solvent;
(b) the external acid is added to the premix obtained in step (a):
(c) an amine is added to the solution obtained in step (b).

Preferably, after step (b) is carried out, the resulting solution is stirred and heated for up to 2 hours, prior to the addition of the amine. According to the inventive process the temperature during mixing and reacting is not higher than 100° C., preferably not higher than 65° C., most preferably no higher than 55° C. The total reaction time generally ranges from about 20 minutes to up to 6 hours.

In the most preferred embodiment of the present invention, an emulsifier is added to the reaction mixture, in order to improve the yield of an N-substituted aldonamide even further. Advantageously, when an emulsifier is an anionic surfactant, the inventive process results in a mixture of nonionic and anionic surfactants which mixture may be used directly as an ingredient in many household and personal care products.

Any N-substituted aldonamide may be synthesized according to the present process, as long as a particular primary or secondary amine $HR^1R^2$ required to produce that aldonamide is available commercially or can be synthesized.

DETAILED DESCRIPTION OF THE INVENTION

The inventive process is suitable for synthesis of any N-substituted aldonamide. Examples of aldonamides include but are not limited to lactobionamides, gluconamides, maltobionamides, cellobionamides, melibionamides, gentiobionamides and the like.

Starting materials employed in the inventive processes include an aldonocompound, a primary or secondary amine carrying the desired Rand groups, an organic polar solvent comprising a solvent having an alcohol functionality, and an external acid. An organic solvent employed in the inventive process must include, at least in part, an organic solvent having an alcohol functionality. Any organic solvent having an alcohol functionality is suitable, for example, aliphatic alcohols, glycols and glycol monoethers, such as methanol, ethanol, propanol, ethylene glycol, polyethylene glycol, triethylene glycol, diethylene glycol, diethylene glycol monoethyl ether, ethylene glycol monobutyl ether, ethylene glycol monoethyl ether, ethylene glycol monomethyl ether, diethylene glycol monobutyl ether, and triethylene glycol monomethyl ether. Of course, other polar solvents not listed above may be employed. According to the present invention, he preferred solvent is selected from the group consisting of primary alcohols (e.g., methanol, ethanol, and propanol). The amount of the organic solvent having an alcohol functionality is at least 3% by weight of the total solvent.

The remainder of the solvent could be any aprotic solvent, dimethylformamide, dimethylsulfoxide, pyridine, acetone. Preferably, the majority of the solvent (i.e., more than 50%), most preferably all the solvent. is an alcohol, which is preferably methanol.

Aldonocompound includes aldonolactones and aldonic acids, and mixtures thereof. Aldonolactone is defined as a lactone of an aldonic acid. Aldonolactone hydrolysis yields aldonic acid. An example of an aldonocompound is as follows:

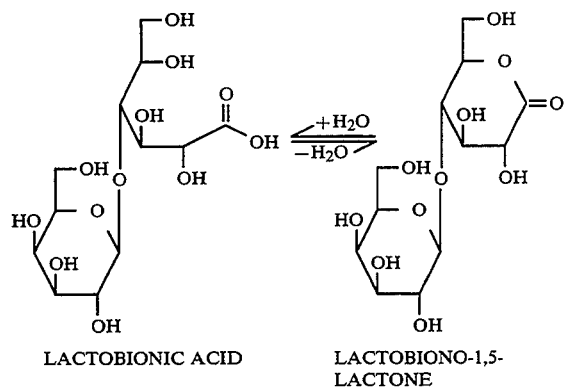

LACTOBIONIC ACID     LACTOBIONO-1,5-LACTONE

Aldonocompounds may be obtained commercially, (e.g., from Aldrich chemicals or from Solvay Deutschland GMBH). The amine, $HNR^1R^2$, may be obtained commercially (e.g., Aldrich chemicals) or it may be synthesized. When aliphatic amines are employed $R^1$ and/or $R^2$ contain at least 3 carbon atoms to ease synthesis (amines wherein $R^1$ and/or $R^2$ contain fewer than 3 carbon atoms have to be bubbled in, due to their high volatility.

According to the inventive process, an external acid is added in order to eliminate or substantially reduce the formation of an ammonium salt during the preparation of the N-alkyl aldonamides.

According to the present invention, suitable external acids include but are not limited to:
Organic Acids: Sulfonic acids (e.g., alkyl benzene sulfonic acid. alkane sulfonic acid, such as methane sulfonic acid, p-toluenesulfonic acid); carboxylic acids (e.g., citric acid, acetic acid, trichloroacetic acid, triflouroacetic acid, glycolic acid, tartaric acid, oxydisuccinic acid, maleic acid); sulfuric acids (e.g., alkyl ether sulfuric acids, alkyl sulfuric acids): phosphoric acids; and mixtures thereof.
Organic Acid Resins: polysulfonic acid type resins (e.g., Amberlite IR 120 ® obtained from Aldrich chemicals Co.)
Inorganic Acids: Lewis acids ($AlCl_3$, $BF_3$, $ZnCl_2$, ZnO, $FeCl_3$, and the like), sulfuric acid, HCl, $H_3PO_4$, and the like, and mixtures thereof.

Mixtures of organic and inorganic acids may be employed.

Preferred external acids are alkyl benzene sulfonic acid, p-toluenesulfonic acid in order to maximize the yield of an N-substituted aldonamide and to minimize the formation of an ammonium salt. The amount of the external acid is critical. If too little acid is used, the formation of an ammonium salt is not sufficiently minimized. The addition of too much acid, however, results in the decomposition of the aldonocompound, thus decreasing the yield of the aldonamide. The amount of the external acid employed in the inventive process ranges from about 0.05% to about 2%, by weight of the aldonocompound and the amine. Preferably from 0.3% to 1% is included in the reaction mixture, in order to attain best results with regard to minimizing or eliminating the formation of an ammonium salt.

In the preferred embodiment of the present process, the order of addition of various ingredients is as follows:
(a) an aldonocompound is premixed with an organic solvent;
(b) an external acid is added to the premix obtained in step (a);
(c) an amine is added to the solution obtained in step (b).

Preferably, after step (b) is carried out, the resulting solution is stirred and heated for up to 2 hours, prior to the addition of the amine. According to the inventive process the temperature during mixing and reacting is not higher than 100° C., preferably not higher than 65° C. and most preferably no higher than 55° C. The total reaction time ranges from about 20 minutes to up to 6 hours.

In the most preferred embodiment of the present invention, an emulsifier is added to the reaction mixture, in order to improve the yield of an aldonamide even further.

Suitable emulsifiers include but are not limited to N-alkyl aldonamides, alkyl benzene sulfonates, ethoxylated alcohols, alkyl ether sulfates, alkyl sulfates, acyl isethionate (e.g., sodium cocoyl isethionate) and alkylpolyglycosides and mixtures thereof.

The preferred emulsifier is N-substituted aldonamide because, unexpectedly, the presence of N-substituted aldonamide in the starting reaction mixture enhances crystallization of the product. Another advantage of using N-substituted aldonamide as an emulsifier when N-substituted aldonamide is synthesized according to the present invention is to maximize the purity of the product; because the very product that is being synthesized is added as an emulsifier, the purity of the product is maximized. According to another aspect of the invention, the inventive process may be employed to make, in-situ, a mixture of an N-substituted aldonamide and another surfactant (anionic and/or nonionic).

Emulsifiers are employed in the inventive process in the amount of from 0.1% to 50% by total weight of an aldonocompound and an amine. Preferably, from 0.1% to 20% and most preferably from 2% to 10% is employed to maximize the yield and the purity of the aldonamide. However, when the in-situ anionic surfactant/aldonamide mixture is prepared the emulsifier amount is preferably high e.g., above 10%, typically in the range of 10% to 50%.

Examples of the reaction employed in the inventive synthesis are as follows:

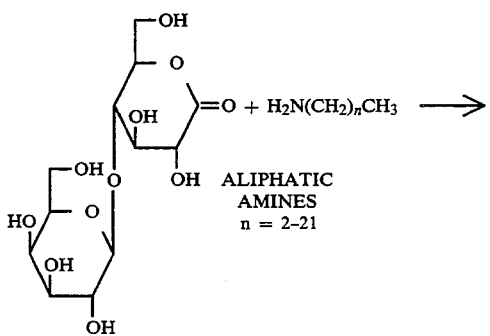

LACTOBIONO-1,5-LACTONE

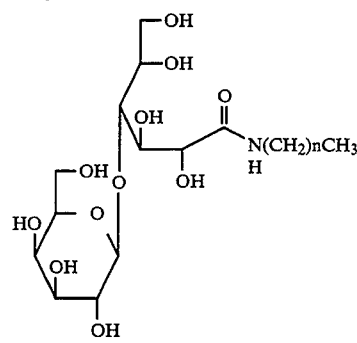

N-ALKYL LACTOBIONAMIDES

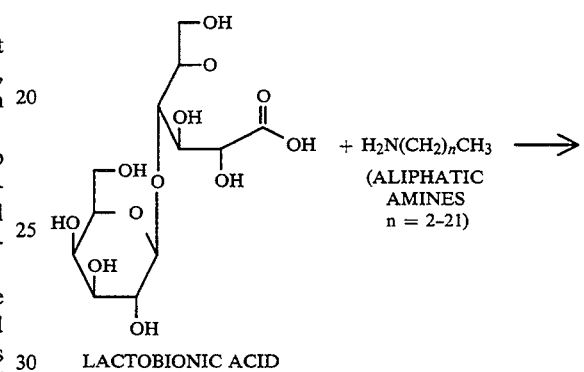

LACTOBIONIC ACID

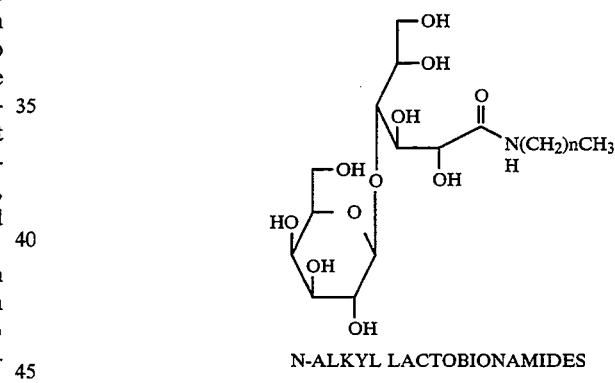

N-ALKYL LACTOBIONAMIDES

The aldonocompound and the amine constitute 10–50% by weight of the starting reaction mixture, and the organic solvent constitutes 50–90% by weight. Preferably, the aldonocompound and the amine constitute from about 15% to about 25% of the starting reaction mixture in order to avoid formation of a viscous phase in the reaction mixture. The molar ratio of the aldonocompound to the amine is typically in the range of from 1.1:1 to 1:1, preferably in the range of from 1:1 to 1:0.96. Most preferably, the molar ratio of the aldonocompound to the amine in the starting reaction mixture is 1:0.93.

In the first step of the inventive process a homogeneous mixture of starting materials is prepared. Preferably, a premix of an aldonocompound and the solvent is prepared first. The acid is subsequently added to the premix. Preferably, in order to facilitate the formation of the homogeneous mixture the solvent is slightly heated, typically to a temperature in the range of from 25° C. to 65° C., preferably in the range of from about 25° C. to 50° C. Most preferably, the premix includes an emulsifier as defined above.

Preferably, the resulting mixture is stirred for at least about 20 minutes, most preferably at least about one hour, optimally at least two hours. The amine, $HNR^1R^2$ is subsequently added with stirring, preferably gradually or in several portions, preferably over the time span of 15 minutes to 2 hours, most preferably over about 30 to 40 minutes in order to attain the homogeneity of the mixture and to optimize the purity of the product. The stirring is conducted with a magnetic stirrer or with an overhead stirrer at moderate rpm. The amine may be added neat (i.e., liquid or melted) or it may be added as a solution in the same solvent that was combined with the aldonocompound. In the preferred embodiment of the invention, the amine is added at a temperature in the range of from 25° C. to 35° C. When an inventive process is employed in a continuous operation, the amine is added continuously.

The resulting homogeneous mixture is reacted to obtain a reaction product including an N-substituted aldonamide. The stirring is typically continued for a period of from 15 minutes to 2 hours; the reaction time depends on the temperature of the reaction and the concentration of starting reactants. The stirring is at the same rate as that employed during the mixing step. The reaction may be conducted at room temperature or at an increased temperature. Typically, the reaction temperature is in the range of from about 25° C. to about 65° C., preferably in the range of from about 25° C. to about 50° C., most preferably in the range of from about 25° C. to about 40° C. It is preferred to carry out the reaction at a temperature not greater than 65° C. in order to minimize heat decomposition as well as base induced elimination. Best results are obtained at temperatures not greater than 60° C., most preferably not greater than 50° C.

Typically, the reaction mixture is continuously heated and the various ingredients are added gradually, with stirring. According to the present invention, the reaction time ranges from 20 minutes to 6 hours, depending on the temperature of the reaction and/or concentration of the reactants.

The product, N-substituted aldonamide, may or may not precipitate out of solution. Typically, at least part of N-substituted aldonamide is present in the solution. When the precipitate is formed, it is separated from the solution. The separation may be conveniently carried out by filtering the precipitate out (by gravity or vacuum filtration), although other separation techniques, e.g. centrifugation, may be employed.

The product, N-substituted aldonamide, is dried. The inventive process typically results in the purity of N-substituted aldonamides above generally at least about 91%. One of the advantages of the inventive process is that the formation of an ammonium salt is substantially decreased or eliminated. Thus, there is no need to separate the salt from the main product of the reaction, the aldonamide.

The inventive process is suitable for batch or continuous operation and any combinations thereof.

In the inventive process, $R^1$ and $R^2$ groups on the starting amine, $HNR^1R^2$ are attached to the nitrogen of an aldonamide. Thus, depending on the particular amine employed, a variety of N-substituted aldonamides may be synthesized according to the inventive process. Preferably, in order to simplify synthesis and reduce cost, $R^1$ is hydrogen, thus a primary amine is employed. $R^1$ and/or $R^2$ generally contain up to 36 carbon atoms. For the sake of clarity, examples of various substituted aldonamides will be given below using lactobionamide of Formula A, maltobionamide of Formula B and gluconamide of Formula C as an illustration. The corresponding ammonium salts of lactobionamide, maltobionamide and gluconamide are illustrated by Formula D, Formula E, and Formula F, respectively.

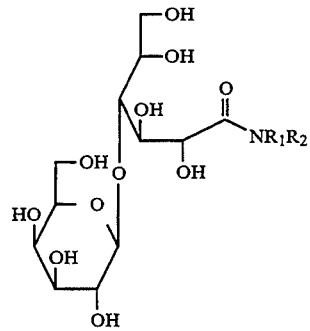

FORMULA A

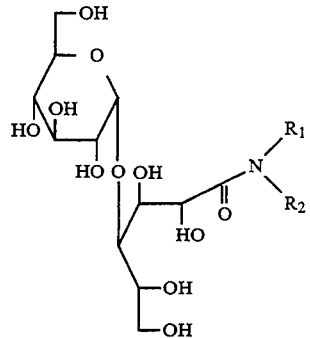

FORMULA B

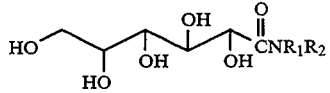

FORMULA C

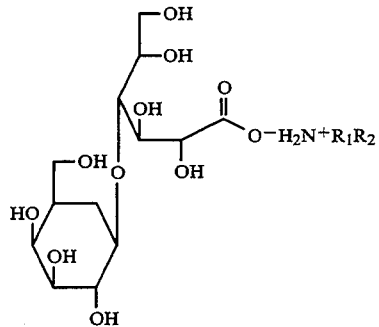

FORMULA D

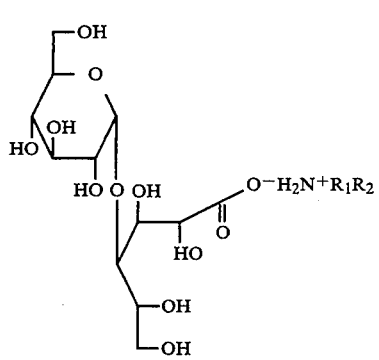

FORMULA E

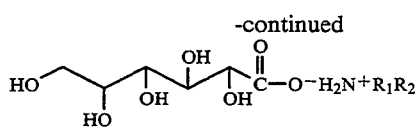

FORMULA F

N-alkyl lactobionamides are compounds of Formula A wherein $R^1$ and/or $R^2$ is an aliphatic hydrocarbon radical (which may include heteroatoms). Suitable aliphatic hydrocarbon radicals include saturated and unsaturated radicals including but not limited to methyl, ethyl, amyl, hexyl, heptyl, nonyl, decyl, undecyl, dodecyl, tridecyl, tetradecyl, pentadecyl, hexadecyl, heptadecyl, and octadecyl, and allyl, undecenyl, oleyl, linoleyl, linolenyl, propenyl, and heptenyl. The active compounds of the inventive compositions may contain straight or branched aliphatic groups. Aromatic radicals are exemplified by benzyl, aniline, or substituted benzyl or aniline groups. Suitable mixed aliphatic aromatic radicals are exemplified by benzyl, phenyl ethyl, phenoxy ethyl, and vinyl benzyl. Cycloaliphatic radicals are exemplified by but not limited to cyclopentyl and cyclohexyl.

N-lactobionyl aminoacid esters include but are not limited to esters of those amino acids which naturally occur in proteins, e.g., alanine, valine, glycine, lysine, leucine, arginine, aspartic acid, glutamic acid, asparagine, glutamine, threonine, serine, cysteine, histidine, tyrosine, methionine, as well as naturally occurring amino acids which are not found in proteins, such as β-alanine, safcosine, gamma-aminobutyric acid, ornithene, citrulline, and the like. An example of N-lactobionyl amino acid ester is when in Formula A $R^1$ is hydrogen and $R^2$ is

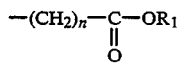

where n is an integer greater than 1 and R is for instance an aliphatic hydrocarbon radical containing up to 36 carbon atoms.

N-(alkyloxy)alkyl lactobionamides are exemplified but not limited to compounds wherein $R^1$ and/or $R^2$ is $-(CH_2)_n-O-R^6$, (an ether connected to amine, i.e., an "ether amine" group) wherein n is an integer equal to or greater than 1, preferably from 1 to 10 and $R^6$ is an aliphatic hydrocarbon radical, an aromatic radical, a cycloaliphatic radical as described above for $R^1$ and $R^2$. Preferably n is from 1 to 3 and $R^6$ is an aliphatic hydrocarbon radical containing 1 to 18 carbon atoms.

N-alkyl lactobionamides, N-(alkyloxy)alkyl lactobionamides and N-lactobionyl aminoacid esters typically contain up to 36 carbon atoms in $R^1$ and $R^2$ groups, preferably up to 24 carbon atoms, most preferably from 8 to 18 carbon atoms, and optimally from 10 to 16 carbon atoms in order to attain optimum surface activity.

N-(polyalkyloxy)alkyl lactobionamides are exemplified by but not limited to compounds wherein $R^1$ and/or $R^2$ is $-R^4-(OR^4)_n-R^4-R^5$ wherein n is an integer greater than 1, $R^4$ is selected from the group consisting of ethylene, propylene, and mixtures thereof; and $R^5$ is an amine or lactobionamide moiety. The number of repeating units in the alkylene oxide radical typically ranges from 2 to 10,000, preferably is from 2 to 100, most preferably from 2 to 10. $R^5$ is preferably lactobionamide (the resulting compound is N-(Polyalkyloxy)alkyl (bis) lactobionamide) in order to provide an additional β-galactose moiety. $R^1$ and/or $R^2$ groups within N-(polyalkyloxy)alkyl lactobionamides may contain heteroatoms; for instance, $R^2$ may be $-CH_2CH_2-S-CH_2CH_2-(OCH_2OCH_2)_n-S-CH_2CH_2-R^5$.

Of course, other $R^1$ and $R^2$ radicals not listed above but within the scope of the claims may be employed.

N-substituted maltobionamides, cellobionamides, melibionamides, gentiobionamides and other aldonamides analogous to N-substituted lactobionamides discussed in detail above may be produced according to the present invention, as long as a particular primary or secondary amine, which is necessary to deliver the desired $R^1$ and/or $R^2$ group to the nitrogen atom of the aldonamide is commercially available or can be synthesized.

The following specific examples further illustrate the present invention, but the invention is not limited thereto.

Lactobionocompounds were obtained from Solvay Deutschland GMBH, external acids (alkyl benzene sulfonic acid, p-toluene sulfonic acid) were obtained from Aldrich. Amines were obtained from Sherex.

Reaction product was analyzed by HPLC:
HPLC apparatus from Waters Co.: Model 600E.
Column: Regis ® Hexyl, 35° C.
Mobile phase: acetonitrile/methanol/water in a ratio of 27.5/27.5/45.
Detector: Waters Model 400 refractive index; 35° C.
Flow Rate: 1.5 ml/min.

EXAMPLE 1

Lactobionocompound (100 g, 1 eq) (lactone:lactobionic acid ratio=8:2) and alkyl benzene sulfonic acid (1.0 g, 0.65% by weight of lactobionocompound and amine) were dissolved in methanol (773.5 g, 50° C.) with sufficient stirring for 20 minutes. Subsequently, cocoamine (54.7 g, 0.93 eq, Adogen-160D ®) was added slowly over 30 minutes, followed by stirring at 45° C. for 15 minutes. The reaction was cooled to room temperature. HPLC analysis indicated that the reaction product contained 97.0% yield of coco lactobionamide with less than 2.0% ammonium salt.

EXAMPLES 2-6

Coco lactobionamides were synthesized using the process described in Example I except that the amount and the identity of an external acid and an emulsifier were varied as indicated in Table 1. In Example 3, no acid was added. The results that were obtained are summarized in Table 1. In Table 1, "LASA" means alkyl benzene sulfonic acid; "PTSA" means p-toluene sulfonic acid.

TABLE 1

| Example | Weight % lactobionocompound and coco amine | % purity lactobionamide | % ammonium salt in reaction product | Weight % External Acid |
|---|---|---|---|---|
| 2 | 20 | 97.0 | 2.0 | 0.65% LASA |
| 3 | 20 | 88.0 | 11.5 | 0.0 |
| 4 | 20 | 96.5 | 1.9 | 0.65% PTSA |
| 5 | 50 | 93.5 | 5.8 | 0.65% LASA |
| 6 | 50 | 94.0 | 4.0 | 0.97% LASA |

The results in Table 1 indicate that in Examples 2, 4, 5 and 6, which are within the scope of the invention, the purity of the aldonamide was substantially improved and the amount of the ammonium salt was substantially decreased compared to Example 3 which is not within the scope of the invention. The results demonstrate the criticality of the inclusion of an external acid into a reaction mixture in order to attain an improved purity of the aldonamide and substantially decrease or eliminate the amount of an ammonium salt in the reaction product.

EXAMPLE 7

Synthesis of Tallow Lactobionamide

Lactobionocompound (100 g, 1 equivalent) and alkyl benzene sulfonic acid (1 g, 0.65% by weight of lactobionocompound and the amine) were dissolved in methanol (400 ml) at 50° C. for 20 minutes. Tallow amine (70 g, 0.93 eq., Adogen 170D ®) was dissolved in 75 ml of methanol and added over 20 minutes. HPLC analysis indicated that the reaction product contained 99% tallow lactobionamide and 1.0% ammonium salt.

EXAMPLE 8

Scaled Up Preparation of Coco Lactobionamide

The reaction was conducted in a 100 gallon glass lined reactor. 62.3 lbs. of lactobionocompound were premixed with 2.07 lbs. of cocolactobionamide (as an emulsifier), and the resulting premix was mixed with 323 lbs. of methanol at room temperature. 0.60 lbs. of dodecyl benzene sulfonic acid was mixed with a small amount (a gallon) of methanol, and the resulting mixture was added to the lactobionocompound/methanol mixture. The resulting mixture was heated, with stirring at 49°-51° C. for two hours. The reaction mixture was cooled to 35° C. Subsequently, 32.8 lbs. of coco amine (predissolved in small quantity of methanol to facilitate its addition to the reactor) were added slowly, with stirring, over a period of 30-40 minutes. After the addition was complete, the stirring was continued for another 20 minutes.

The reaction product solution was cooled down to room temperature and held for 16 hours to complete crystallization. The solution was then centrifuged, and the obtained filter cake was vacuum dried. Fifty two pounds of coco lactobionamide were obtained. The purity of the lactobionamide was 96%. The product contained 1.1% of an ammonium salt.

Examples 9-12 further demonstrate the preparation of N-Substituted lactobionamides according to the present invention.

EXAMPLE 9

15.0 g of lactobionocompound were charged into a 150 ml flask. 100 ml of methanol were added at 25° C. The batch was heated up to 50° C. 0.15 g of alkyl benzene sulfonic acid were charged into the reaction vessel. After this addition the mixture was held at 50° C. for 1 hour. 8.2 g of cocoamine were added at 50° C. in 30 minutes. The batch was then cooled down to 25° C. in 30 minutes and left overnight for crystallization. 19 g of white crystaline product were recovered after filtration. A sample was taken for HPLC analysis.

EXAMPLE 10

15.0 g of lactobionocompound were charged into a 150 ml flask. 100 ml of methanol were added at 25° C. The batch was heated up to 50° C. 0.95 g of alkyl benzene sulfonic acid were charged into the reaction vessel. After this addition the mixture was held at 50° C. for 1 hour. 8.2 g of cocoamine were added at 50° C. in 30 minutes. The batch was then cooled down to 25° C. in 30 minutes and left overnight for crystallization. 19 g of white crystaline product were recovered after filtration. A sample was taken for HPLC analysis.

EXAMPLE 11

Into 100 ml flask was placed 50 ml of methanol and 0.04 g of alkyl benzene sulfonic acid. 5 g of lactobionocompound were dissolved in this mixture at 50° C. After 2 hour hold at 50° C. the reaction mixture was cooled down to 25° C. 2.5 g of cocoamine were added in 2 hours. Lactobionamide was recovered by filtration after overnight crystallization. A sample was taken for HPLC analysis.

EXAMPLE 12

Into 200 ml flask was placed 100 ml of methanol and 0.14 g of alkyl benzene sulfonic acid. 15 g of lactone were dissolved in this mixture at 50° C. After 2 hour hold at 50° C. reaction mixture was cooled down to 35° C. 7.9 g of cocoamine predissolved in 15 ml of methanol were added in 35 minutes. After 20 minutes hold reaction mixture was cooled down to 25° C. and left overnight for crystallization. Lactobionamide was recovered by filtration, A sample was taken for HPLC analysis.

Table 2 summarizes Examples 9-12 and results of products' analyses,

TABLE 2

| Example | Weight % of Lactobionocompound and Amine | % Purity of Lactobionamide | % Ammonium Salt in Reaction Product | Weight % External Acid |
|---|---|---|---|---|
| 9 | 22 | 91 | 4.0 | 0.65 |
| 10 | 22 | 85 | 9.0 | 4.00 |
| 11 | 22 | 94 | 1.1 | 0.65 |
| 12 | 22 | 97 | 0.8 | 0.65 |

The results in Table 2 indicate that the concentration of acid is critical in order to attain the N-substituted aldonamide of improved purity and to minimize the formation of an ammonium salt. Specifically, Examples 9, 11 and 12 wherein the concentration of the external acid was less than 2% resulted in improved purity (i.e., >90%) of the aldonamide, compared to Example 10 which utilized 4% of the external acid. It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A process of preparing an N-substituted aldonamide, the process comprising the steps of:
   i) preparing a homogeneous mixture comprising an aldonocompound, from about 0.05% to about 2% by total weight of an aldonocompound and an amine of an external acid, an organic polar solvent comprising a solvent having an alcohol functionality, and an amine $HNR^1R^2$, wherein $R^1$ and $R^2$ are the same or different and may contain heteroatoms and are selected from the group consisting of hydrogen, an aliphatic hydrocarbon radical, an aromatic radical, a cycloaliphatic radical, an amino acid ester, an ether amine and mixtures thereof, except that $R^1$ and $R^2$ are not both hydrogen at the same time, and ii) reacting the homogeneous mixture at a temperature not greater than 100° C. to obtain the aldonamide.

2. The process of claim 1 wherein the aldonocompound is selected from the group consisting of an aldonolactone, an aldonic acid, and mixtures thereof.

3. The process of claim 1 wherein the external acid selected from he group consisting of organic acids, organic acid resins, inorganic acids, and mixtures thereof.

4. The process of claim 1 wherein the homogeneous reaction mixture further comprises an emulsifier.

5. The process of claims wherein the amount of the emulsifier is in the range of from 0.1% to 50%.

6. The process of claim 1 wherein step (i) of the process comprises premixing the aldonocompound with the external acid, dissolving the obtained premix in the organic polar solvent and subsequently, adding the amine.

7. The process of claim 1 wherein the mixing is conducted at a temperature in the range of from 25° C. to 65° C.

8. The process of claim 1 wherein the aldonocompound is a mixture of lactobiono-1,5-lactone and lactobionic acid.

9. The process of claim 1 wherein the reaction in step (ii) is conducted at a temperature in the range of 25 to 65° C.

10. The process of claim 1 wherein the reaction in step (ii) is conducted at a temperature not greater than 50° C.

11. The process of claim 1 wherein $R^1$ is hydrogen.

12. The process of claim 1 wherein the aldonamide is selected from the group consisting of lactobionamides, gluconamides, maltobionamides, cellobionamides, melibionamides, and gentiobionamides.

13. The process of claim 1 wherein $R^1$ and $R^2$ are the same or different and both together include from 1 to 36 carbon atoms.

14. The process of claim 1 wherein the iodine value of $R^1$ and $R^2$ is no greater than 12.

15. The process of claim 1 wherein the molar ratio of the aldonolactone to the amine is in the range of from about 1.1:1 to about 1:1.

16. The process of claim 1 wherein the solvent comprising an alcohol functionality is present in the amount of at least 3% by weight of the total solvent.

17. The process of claim 1 wherein the solvent having an alcohol functionality is selected from the group consisting of methanol and ethanol.

18. An in-situ process of preparing a mixture of an N-substituted aldonamide and at least one surfactant selected from the group consisting of a nonionic surfactant and an anionic surfactant, the process comprising:

(i) preparing a homogeneous mixture comprising an aldonocompound, from about 0.05% to about 2% by total weight of an aldonocompound and an amine of an external acid, an organic polar solvent comprising solvent having an alcohol functionality, the surfactant, and an amine $HNR^1R^2$, wherein $R^1$ and $R^2$ are the same or different and may contain heteroatoms and are selected from the group consisting of hydrogen, an aliphatic hydrocarbon radical, an aromatic radical, a cycloaliphatic radical, an amino acid ester, an ether amine and mixtures thereof, except that $R^1$ and $R^2$ are not both hydrogen at the same time, and (ii) reacting the homogeneous mixture at a temperature not greater than 100° C. to obtain the mixture of the aldonamide and the surfactant.

19. The process of claim 18 wherein step (i) of the process comprises premixing the aldonocompound with the external acid, dissolving the obtained premix in the organic polar solvent, adding the surfactant, and subsequently, adding the amine.

20. The process of claim 18 wherein the surfactant is an anionic surfactant.

21. The process of claim 20 wherein the anionic surfactant is selected from the group consisting of alkyl benzene sulfonates, alkyl ether sulfates, alkyl sulfates, acyl isethionates, and mixtures thereof.

* * * * *